US012806154B2

(12) United States Patent
Loper et al.

(10) Patent No.: US 12,806,154 B2
(45) **Date of Patent: *Nov. 24, 2026**

(54) COMPOSITION, SYSTEM AND METHOD FOR A PIG CONTRACEPTIVE

(71) Applicant: Corona Feed Additives, L.L.C., Clovis, NM (US)

(72) Inventors: Daniel August Loper, Clovis, NM (US); Daniel Carl Loper, Clovis, NM (US); Bradley Dean Fails, Dublin, TX (US)

(73) Assignee: CORONA FEED ADDITIVES, L.L.C., Clovis, NM (US)

( * ) Notice: Subject to any disclaimer, the term of this patent is extended or adjusted under 35 U.S.C. 154(b) by 1015 days.

This patent is subject to a terminal disclaimer.

(21) Appl. No.: 17/722,120

(22) Filed: Apr. 15, 2022

(65) Prior Publication Data

US 2022/0233467 A1 Jul. 28, 2022

Related U.S. Application Data

(63) Continuation-in-part of application No. PCT/US2021/024248, filed on Mar. 25, 2021.

(Continued)

(51) Int. Cl.
*A61K 31/11* (2006.01)
*A23K 10/30* (2016.01)

(Continued)

(52) U.S. Cl.
CPC .............. *A61K 31/11* (2013.01); *A23K 10/30* (2016.05); *A23K 10/33* (2016.05); *A23K 50/30* (2016.05); *A61K 9/0056* (2013.01)

(58) Field of Classification Search
CPC ...... A61K 31/11; A61K 47/46; A61K 9/0056; A61K 9/2054; A61K 9/2009; A61K 9/2018; A61K 9/2059; A61K 9/1652; A61K 2300/00; A61K 31/4045; A61K 9/2095; A61K 31/455; A61K 45/06; A61K 47/12; A61K 9/2013; A61K 31/198; A61K 31/355; A61K 31/375; A61K 36/00; A61K 38/00; A61K 47/38; A61K 9/0053; A61K 9/14; A61K 9/1617; A61K 9/2866; A61K 9/5089; A61K 2035/115; A61K 31/10; A61K 31/352; A61K 31/4415; A61K 31/51; A61K 31/665; A61K 31/7008; A61K 31/714; A61K 31/726; A61K 31/728; A61K 31/737; A61K 33/00; A61K 33/06; A61K 33/32; A61K 35/00; A61K 38/06; A61K 47/32; A61K 8/19; A61K 8/24; A61K 8/922; A61K 8/9789; A61K 8/9794; A61K 8/986; A61K 9/1694; A61K 9/4891; A61K 9/0007; A61K 9/20; A61K 9/2081; A61K 31/506; A61K 31/565; A61K 31/585; A61K 47/26; A61K 9/00; A61K 9/2077; A61K 9/286; A61K 9/5047; A61K 31/14; A61K 31/192; A61K 31/445; A61K 31/465; A61K 31/55; A61K 31/57; A61K 9/0058; A61K 9/0065; A61K 9/146; A61K 9/1623; A61K 9/1635; A61K 9/2027; A61K 9/284; A61K 9/2886; A61K 9/5026; A61K 31/05; A61K 31/07; A61K 31/12; A61K 31/13; A61K 31/135; A61K 31/185; A61K 31/215; A61K 31/216; A61K 31/24; A61K 31/404; A61K 31/422; A61K 31/437; A61K 31/439;

(Continued)

(56) References Cited

U.S. PATENT DOCUMENTS

| | | |
|---|---|---|
| 4,297,341 A | 10/1981 | Waller et al. |
| 4,381,298 A | 4/1983 | Coulson |

(Continued)

FOREIGN PATENT DOCUMENTS

| | | |
|---|---|---|
| CN | 1179647 C | 12/2004 |
| CN | 102187881 A | 9/2011 |

(Continued)

OTHER PUBLICATIONS

Randel, Ronald. "Effects of gossypol and cottonseed productiosn on reproduction of mammals", Journal of Animal Science; J Anim Sci 1992, 70:1628-1638. (Year: 1992).*

Randel et al., "Effects of gossypol and cottonseed products on reproduction of mammals", Journal of Animal Science, vol. 70, Issue 5, May 1992, pp. 1628-1638. (Year: 1992).*

Baccetti, Baccio, et al. "The action of gossypol on rat germinal cells." Gamete research 13.1 (1986): 1-17.

Pan, Lester C., Mathew J. Nadakavukaren, and D. Reed Jensen. "Effects of ingested gossypol on the ultrastructure of rat ovarian follicles." Cell and tissue research 250.1 (1987): 215-220.

(Continued)

*Primary Examiner* — Audrea B Coniglio

(74) *Attorney, Agent, or Firm* — James R. Gourley; Stephanie E. Scoggin; Carstens, Allen & Gourley, LLP

(57) ABSTRACT

An orally ingestible contraceptive composition for a pig is provided. The exemplary composition comprises 0.005 to 1.4 wt. % free gossypol and non-free-gossypol matter. The non-free-gossypol matter comprises a bulk feed component, a pig attractant, a flavored component or any combination thereof. In a second aspect, an assembly is provided. The assembly comprises an orally ingestible contraceptive composition for a pig and a package. In a third aspect, a system for delivering an orally ingestible contraceptive composition to a pig is provided. The system comprises the composition and an apparatus. The apparatus is configured to permit pigs to eat the composition and inhibit other animals from eating the composition. In a fourth aspect, a method is provided for delivering an orally ingestible contraceptive composition to a pig. The method comprises making the composition available to the pig.

10 Claims, 4 Drawing Sheets

Related U.S. Application Data

(60) Provisional application No. 63/033,102, filed on Jun. 1, 2020.

(51) Int. Cl.
*A23K 10/33* (2016.01)
*A23K 50/30* (2016.01)
*A61K 9/00* (2006.01)

(58) Field of Classification Search
CPC ...... A61K 31/451; A61K 31/46; A61K 31/53; A61K 31/5375; A61K 31/541; A61K 31/5415; A61K 31/551; A61K 31/56; A61K 31/567; A61K 31/722; A61K 35/12; A61K 35/742; A61K 36/28; A61K 36/48; A61K 36/53; A61K 36/54; A61K 36/61; A61K 36/67; A61K 36/71; A61K 36/88; A61K 36/9066; A61K 36/9068; A61K 38/40; A61K 38/43; A61K 38/47; A61K 47/02; A61K 47/42; A61K 47/6951; A61K 9/0004; A61K 9/0095; A61K 9/145; A61K 9/2072; A61K 9/28; A61K 9/2853; A61K 9/48; A61K 9/4808; A61K 9/4816; A61K 9/4825; A61K 9/485; A61K 9/4858; A61K 9/5005; A61K 9/5015; A61K 9/5031; A61K 9/5042; A61K 9/5078; A61K 9/5084; A61P 25/00; A61P 25/16; A61P 15/00; A61P 1/00; A61P 25/18; A61P 25/24; A61P 25/28; A61P 25/34; A61P 1/06; A61P 1/08; A61P 1/12; A61P 1/14; A61P 1/18; A61P 25/04; A61P 25/06; A61P 25/08; A61P 25/14; A61P 29/00; A61P 7/02; A61P 9/00; A61P 9/14
See application file for complete search history.

(56) References Cited

U.S. PATENT DOCUMENTS

| | | | | |
|---|---|---|---|---|
| 5,112,637 | A | 5/1992 | Hron, Sr. et al. | |
| 5,270,062 | A | 12/1993 | Buchs | |
| 6,192,831 | B1 * | 2/2001 | Brunse | A01K 5/0225 119/61.2 |
| 6,212,819 | B1 | 4/2001 | Edwards | |
| 6,773,727 | B1 | 8/2004 | Rojas et al. | |
| 7,342,046 | B2 | 3/2008 | Wang et al. | |
| 8,455,540 | B2 | 6/2013 | Mortier et al. | |
| 8,962,058 | B2 | 2/2015 | Prakash et al. | |
| 2005/0037200 | A1 | 2/2005 | Wallach | |
| 2006/0008512 | A1 | 1/2006 | Hooge | |
| 2007/0116838 | A1 | 5/2007 | Prakash et al. | |
| 2008/0021110 | A1 | 1/2008 | Wang et al. | |
| 2008/0233244 | A1 * | 9/2008 | Swenson | A23J 3/26 426/72 |
| 2009/0285865 | A1 | 11/2009 | Shalaby | |
| 2010/0069344 | A1 | 3/2010 | Wang et al. | |
| 2013/0324608 | A1 * | 12/2013 | Pan | A61P 25/02 514/560 |
| 2016/0183494 | A1 | 6/2016 | Wammock | |
| 2019/0328004 | A1 | 10/2019 | Johnson et al. | |
| 2020/0359653 | A1 | 11/2020 | Johnson et al. | |
| 2022/0227869 | A1 | 7/2022 | Duvaux et al. | |
| 2022/0233467 | A1 | 7/2022 | Loper et al. | |

FOREIGN PATENT DOCUMENTS

| | | | |
|---|---|---|---|
| CN | 110024815 | A | 7/2019 |
| WO | 2007074478 | A1 | 7/2007 |
| WO | 2009013405 | A2 | 1/2009 |
| WO | 2011081208 | A1 | 7/2011 |

OTHER PUBLICATIONS

Randel et al., "Effects of gossypol and cottonseed products on reproduction of mammals", Journal of Animal Science, (May 1, 1992), vol. 70, No. 5, pp. 1628-1638, XP055883530.
Akinola, Ob, et al., "Proteinaceous diet inhibits gossypol-induced spermatotoxicity", European Journal of Histochemistry (2006) 50(3):205-208 (4 pages).
Alexander, J, et al., Panel Members. "Gossypol as undesirable substance in animal feed. Scientific Opinion of the Panel on Contaminants in the Food Chain (Question No. EFSA-Q-2005-222)", The European Food Safety Authority Journal (2008) 908, 1-55 (55 pages).
Chenoweth et al., "Effects of dietary gossypol on aspects of semen quality, sperm morphology and sperm production in young Brahman bulls", Theriogenology, 1994; 42: 1-13 (13 pages).
Examination Report No. 1 for AU Application No. 2022291611 dated Mar. 19, 2024 (7 pages).
Extended European Search Report for EP Application No. 21816765.8 dated Jul. 4, 2024 (7 pages).
Gizejewski et al., "Cottonseed feeding delivers sufficient quantities of gossypol as a male deer contraceptive", European Journal of Wildlife Research, Feb. 13, 2008; 54: 469-477 (9 pages).
Tso, et al., "Gossypol uncoupling of respiratory chain and oxidative phosphorylation in ejaculated boar spermatozoa", Contraception, Jun. 1, 1982; 25(6): 649-655 (7 pages).
Argo Feeds, Rat and Mouse Cubes, [retrieved from the Internet on Nov. 15, 2024] Published Mar. 29, 2019 (2 pages).
Examination Report No. 2 for Australian patent application No. 2022291611 dated Nov. 15, 2024 (7 pages).
Harmon, B.G., et al., "Molasses/Fat Combination as a Nutrient Source for Swine," Purdue University 1998 Swine Day Report (5 pages).
Eisele, GR, A Perspective on Gossypol Ingestion in Swine, Veterinary and Human Toxicology, Apr. 1986, 28, 118-112 (5 pages).
Katoh, Noria, et al., "Inhibition by Gossypol of Cyclic Nucleotide-independent Phosvitin Kinase from Pig Testis," Japanese J. of Veterinary Science, 51, 105-109, 1989, DOI: https://doi.org/10.1292/jvms1939.51.105 (5 pages).
Kobayashi, Haruo, et al., "Male Sterility Effect of Cottonseed Oil Component, Gossypol," J. of Japan Veterinary Medical Ass'n, 41, 1988, 594-597, DOI: 10.12935/jvma1951.41.594 (4 pages).
Martin, Steve D., "Gossypol effects in animal feeding can be controlled," Feedstuffs, Apr. 6, 1990, 62, 14-15 (2 pages).

* cited by examiner

COMPOSITION, SYSTEM AND METHOD FOR A PIG CONTRACEPTIVE

CROSS-REFERENCE TO RELATED APPLICATIONS

This application is a continuation-in-part of, and claims priority to, PCT Application No. PCT/US2021/024248, entitled "COMPOSITION, SYSTEM AND METHOD FOR A PIG CONTRACEPTIVE," filed Mar. 25, 2021 and published as WO/2021/247124 on Dec. 9, 2021, which claims priority to US Provisional Application No. 63/033,102, entitled "COMPOSITION, SYSTEM AND METHOD FOR A PIG CONTRACEPTIVE," and filed on Jun. 1, 2020. Each application, publication, and patent listed in this paragraph is hereby incorporated by reference as an example.

BACKGROUND

Technical Field

Embodiments of the present invention relate to compositions, systems, and methods for controlling the wild or feral pig population through decreased fertility.

Background

The wild hog population has been growing for years, and is now out of control. Large amounts of damage to farms, ranches, beaches, golf courses, etc., are observed every year and it's getting worse.

Sows can give birth to two to three litters per year of fourteen to twenty four baby pigs per year so they populate a farm or ranch rapidly.

SUMMARY OF THE INVENTION

In a first aspect, an orally ingestible contraceptive composition for a pig is provided. The exemplary composition comprises 0.005 to 1.4 wt. % free gossypol and non-free-gossypol matter. The non-free-gossypol matter comprises a bulk feed component, a pig attractant, a flavored component or any combination thereof.

In a second aspect, an assembly is provided. The assembly comprises an orally ingestible contraceptive composition for a pig and a package.

In a third aspect, a system for delivering an orally ingestible contraceptive composition to pigs is provided. The system comprises the composition and an apparatus. The apparatus is configured to permit pigs to eat the composition and inhibit other animals from eating the composition.

In a fourth aspect, a method is provided for delivering an orally ingestible contraceptive composition to a pig. The method comprises making the composition available to the pig.

Other aspects, embodiments and features of the invention will become apparent from the following detailed description of the invention when considered in conjunction with the accompanying drawings. The accompanying figures are schematic and are not intended to be drawn to scale. In the figures, each identical, or substantially similar component that is illustrated in various figures is represented by a single numeral or notation. For purposes of clarity, not every component is labeled in every figure. Nor is every component of each embodiment of the invention shown where illustration is not necessary to allow those of ordinary skill in the art to understand the invention.

BRIEF DESCRIPTION OF THE DRAWINGS

Novel features believed to characteristic of the claimed embodiments of the invention are set forth in the appended claims. The invention itself, however, as well as a preferred mode of use, further objectives and advantages thereof, will be best understood by reference to the following detailed description of illustrative embodiments when read in conjunction with the accompanying drawings, wherein:

DETAILED DESCRIPTION

Pigs, as used herein, refers to any member of the Suidae family, whether wild or domesticated, and including animals that are commonly referred to as pigs, swine, boars, and hogs. A new composition is provided that can be used, for example, as a pig contraceptive, The composition can be useful to stop the undesired reproduction of wild pigs, domestic pigs, feral pigs or any combination thereof. By way of illustration, the composition can be a mixture of natural feedstuffs that is fed to feral hogs to reduce the number of feral hogs on a farm, ranch, or property. Advantageously, the composition can act as a male contraception for feral boar hogs, reducing viable sperm counts in feral boar hogs, and, hence, reducing the fertility of the feral boar hogs. Accordingly, the births of baby pigs can be decreased and feral hog populations can be decreased over time.

Figure 1:
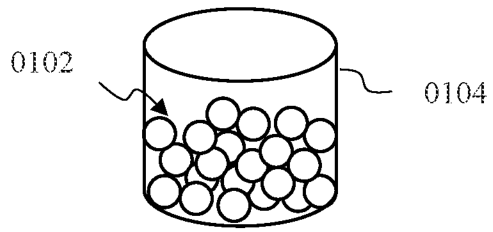
FIG. 1 is a schematic illustration of an embodiment of an orally ingestible contraceptive composition for a pig, the composition being located in a container.

With reference now to FIG. 1, an example of an orally ingestible contraceptive composition 0102 for a pig is illustrated. The composition is located in a container 0104.

Figure 2:
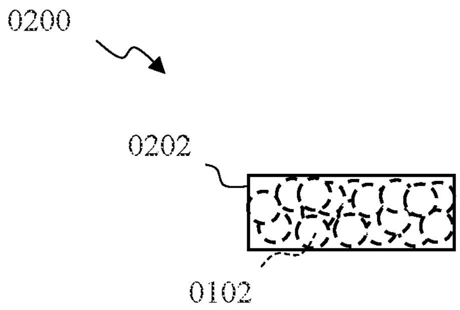
FIG. 2 is a schematic illustration of an assembly comprising an orally ingestible contraceptive composition for a pig and a package.

Also disclosed is an assembly 0200 comprising the composition 0102 and a package 0202, for example, as illustrated in FIG. 2.

Figure 3:
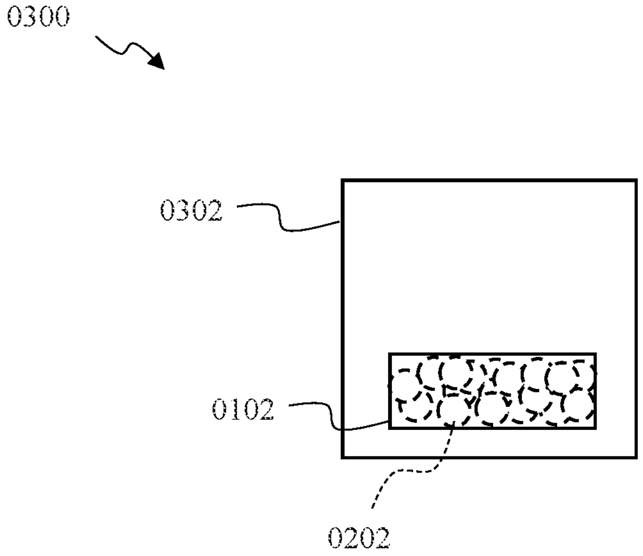
FIG. 3 is a schematic illustration of an embodiment of a system for delivering an orally ingestible contraceptive composition to a pig, the system comprising an orally ingestible contraceptive composition and an apparatus configured to permit pigs to eat the composition and inhibit other animals from eating the composition.

Turning now to FIG. 3, this figure depicts a schematic illustration of a system 0300 for delivering an orally ingestible contraceptive composition 0102 to a pig. The system 0300 comprises the composition 0102 and an apparatus 0302 configured to permit pigs to eat the composition and inhibit other animals from eating the composition. As illustrated, the composition is provided as part of an assembly including package 0202. However, as a skilled person would understand, the composition can be provided inside the apparatus 0302 without a package to contain the composition or the composition can be provided inside the apparatus 0302 in a package that contains the composition.

Figure 4:
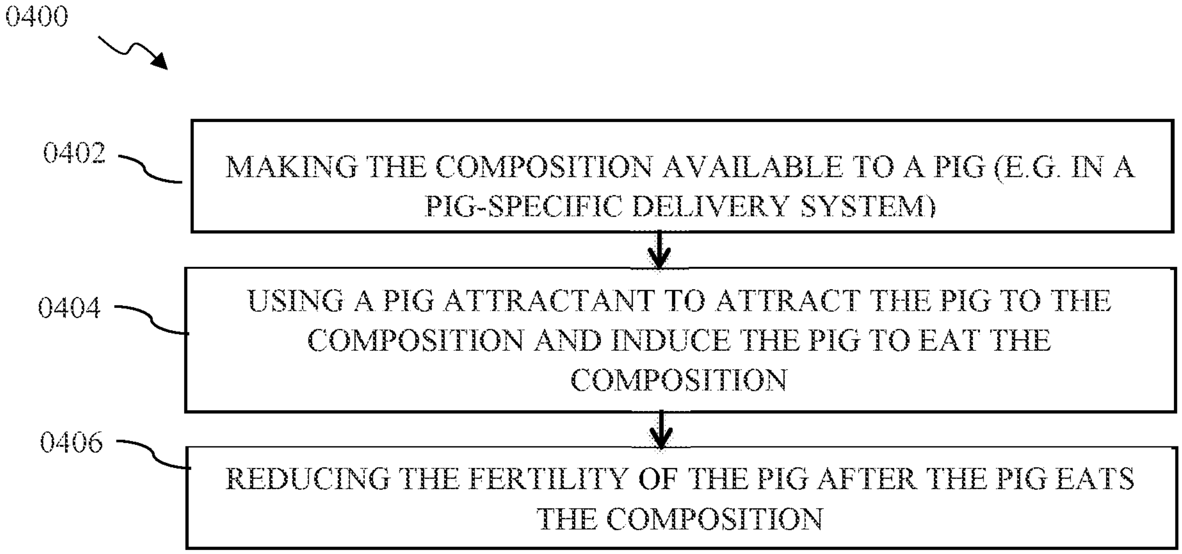
FIG. 4 is a schematic flow chart illustrating an embodiment of a method for delivering an orally ingestible contraceptive composition to a pig.

With reference now to FIG. 4, a schematic flow chart illustrates an embodiment of a method 0400 for delivering an orally ingestible contraceptive composition to a pig. The method comprises several steps. A first step comprises making 0402 the composition available to a pig, for example, in a pig-specific delivery system. In some embodiments, making the composition available to a pig is part of a step of making an assembly available to the pig, the assembly comprising the composition.

In some embodiments, a second step comprises using 0404 a pig attractant to attract the pig to the composition and induce the pig to eat the composition. This second step can occur before the first step, during the first step, after the first step, or any combination thereof. For example, the pig attractant can be a component of the composition.

As illustrated, a third step can comprise reducing 0406 the fertility of the pig after the pig eats the composition. The third step can occur after the first step, after the second step or after both steps.

EXPERIMENTAL EXAMPLE

A 30-day feeding trial was conducted in Erath County, Texas in the spring of 2018 to study the effect of the novel contraceptive composition, a formulated feral hog feed, on male reproductive performance. All hogs were fed 3 lbs of feed per head per day. The contraceptive composition consisted of 1080 lbs corn (fine ground), 800 lbs cottonseed meal, 100 lbs molasses, and 20 lbs salt. A commercially available feed for hogs was fed to the control group. There were three treatment groups. Treatment groups were fed the novel contraceptive according to Table 1.

TABLE 1

| Boar # | Protocol Description | Total Days | Motility Score | Morphology Score |
|---|---|---|---|---|
| 1 | For each of 5 consecutive days, boar # 1 was fed the contraceptive composition; then for each of 25 consecutive days, boar # 1 was fed commercial hog feed | 30 | ~40% | <30% (Predominant morphological abnormalities consisted of sharp bent tails) |
| 2 | For each of 15 consecutive days, boar # 2 was fed the contraceptive composition; then for each of 15 consecutive days, boar # 2 was fed commercial hog feed | 30 | ~50% | ~50% (Predominant morphological abnormalities consisted of distal droplets on tail and sharp bent tails) |
| 3 | For each of 30 consecutive days: boar # 3 was fed the contraceptive composition | 30 | <30% | <40% (Predominant morphological abnormalities consisted of sharp bent tails, distal droplets, and detached heads) |
| 4 | Control: for each of 30 consecutive days: boar # 4 was fed commercial hog feed without being fed the contraceptive composition | 30 | >70% (very good) | ~80% (Predominant morphological abnormalities consisted of sharp bent tails and distal droplets on tail) |

For the experiment whose results are reported in Table 1, Boars 1, 2, 3 and 4 were fed the novel contraceptive composition for 5 days, 15 days, 30 days, and not at all, respectively, during the 30-day trial. Each hog, based on their feeding schedule, was fed the novel contraceptive composition consecutively starting on day one, then switched to commercially available hog feed when indicated. The hogs used in the experiment had all previously been used as breeding sires and were of viable breeding age and health. Semen was collected at the end of the 30-day trial and the animals were then slaughtered. For the semen collected from each boar, a veterinarian conducted a semen evaluation by looking at a representative sample of the semen under magnification. The results of the semen studies demonstrated that all hogs that were fed the novel contraceptive feed had less than or equal to approximately 50% sperm motility and less than or equal to approximately 50% morphology scores, reducing their reproductive abilities. The sperm motility and morphology scores are based on a percentage of the total number of sperm evaluated. Previous research into swine reproduction has shown a motility score of more than or equal to 70% and morphology score of more than or equal to 80% is required for a sperm to be viable. It was of particular interest to note that the hogs that had only received the novel contraceptive for five days out of 30 days had the same reduced reproductive potential as the 15 day and 30-day treatments. All groups readily consumed the feed daily based on their individual feed schedules. All hogs were kept in separate, side-by-side, half-shaded pens during the complete experiment. These results are encouragement that feral hog damages to farm crops and property may be greatly reduced in the future by negatively impacting male feral hog reproductive performance by feeding non-toxic, all-natural feeds such as a contraceptive composition described in this disclosure.

In some embodiments, a composition comprising the contraceptive is configured to be shelf stable for up to 6 months in dry storage place. In some embodiments, a composition comprising the contraceptive is configured to be stable in wild pig only feeder for at least one, two, three or fourth months without exposure to direct sunlight, water, rain, or flowing water. As an example, a stable composition remains effective to render a male pig sterile upon eating 3 pounds of contraceptive per pig per day for 3 days in a one month time period, where the days are optionally consecutive, non-consecutive or either consecutive or non-consecutive. As an example, a pig can be deemed sterile if the pig has a sperm motility score of 0% to less than 70%, 65%, 60%, 55%, 50%, 45%, 40%, 35% or 30%; a sperm morphology score of 0% to less than 80%, 75%, 70%, 65%, 60%, 55%, 50%, 45%, 40%, 35%, or 30%; or a combination thereof.

In some embodiments, a composition comprising the contraceptive is a dry food with a low moisture content, for example, 10-40%, 10-30%, 10-20% or 10-15% moisture by weight.

In some embodiments, the composition comprising a contraceptive can be used with =an apparatus configured to permit pigs to eat the composition and inhibit other animals from eating the composition. An example of such an apparatus is a hog feeder, for example, any hog feeder described in U.S. Pat. No. 10,034,454 B2, issued Jul. 31, 2018, published as US 2016/0183494 A1 on Jun. 30, 2016, which are all hereby incorporated by reference in their entirety as examples. As described in U.S. Pat. No. 10,034,454, the feeder can be configured to prevent access to an edible composition by non-hoofed animals. Therefore, pigs, which have hooves, can access the edible composition but other animals, for example, bears, cannot access the edible composition within the housing. The feeder described in U.S. Pat. No. 10,034,454 is also an example of a wild pig specific delivery system. Of course, the feeder described in U.S. Pat. No. 10,034,454 is merely an example and the methods, compositions and systems described in the present disclosure can also be used with any suitable wild pig specific delivery system that is currently available. For example, the wild pig specific delivery system can be any system that is approved by the entity with jurisdiction over the area where the system will be used.

ILLUSTRATIVE EXAMPLES

Illustrative embodiments of the present invention include, but are not limited to:

Example 1. A food-stuff that reduces the mobility and morphology of sperm in feral male boar hogs, comprising, consisting essentially of, or consisting of (i) any composition described in a claim, or additional embodiment clause in this application or (ii) gossypol as part of, or in combination with all or any selection of the ingredients listed in Table 2, with each ingredient being present in the food-stuff at a concentration or any range of concentrations equal to or contained within the ranges of concentrations listed in Table 2.

Example 2. The food-stuff of example 1, wherein the food-stuff is configured so that the consumption of the food-stuff by male feral boar hogs: (i) reduces the fertility of the male feral boar hogs significantly in an area where the food-stuff is placed, (ii) decreases births of baby pigs in the area where the food-stuff is placed, (iii) decreases feral hog populations over time in the area where the food-stuff is placed, or (iii) any combination thereof.

Example 3. A method of delivering the food-stuff of any one of Example 1 and 2, the method comprising delivering the food-stuff through a wild pig specific delivery system.

Example 4. A method of delivering the food-stuff of any one of Example 1 and 2, the method comprising delivering the food-stuff through a system configured to permit access to wild pigs and deny access to other animals.

A method of delivering the food-stuff of any one of Example 1 and 2, the method comprising delivering the food-stuff through a wild pig specific delivery system.

TABLE 2

| Component | Concentration Range (lbs of Component per ton of Total Composition |
|---|---|
| Either: | 0.8 lbs to 2.4 lbs/ton or 0.005 to 0.12 wt. % |
| (i) Gossypol (e.g., Free Gossypol, which can be from Cottonseed Meal or Oil, the gossypol and free gossypol also referred to herein as Cottonseed Extract because gossypol is an example of Cottonseed Extract) or (ii) Cottonseed Meal comprising Gossypol (e.g., Free Gossypol) | 100 to 1200 lbs/ton or 5 to 60 wt. % |
| Corn | 100 to 1500 lbs/ton or 5 to 75 wt. % |
| Molasses | 10 to 100 lbs/ton or 0.5 to 5 wt. % |
| Salt | 10 to 80 lbs/ton or 0.5 to 4 wt. % |
| Apple Flavor | 1 to 15 lbs/ton or 0.05 to 0.75 wt. % |
| Dried sour corn mash | 5 to 500 lbs/ton or 0.25 to 25 wt. % |
| One or more additives | Variable |
| One or more flavored components | Variable |
| One or more extracts | Variable |
| One or more attractants (e.g., pig pheromone, scented components, or any combination thereof) | Variable |

Note:
for Table 2, 1 ton is 2000 lbs.

ADDITIONAL EMBODIMENTS

The following clauses are offered as further description of embodiments of the compositions, systems, and methods disclosed herein:

1. An orally ingestible contraceptive composition for a pig (e.g., male pig, female pig, or male and female pigs) comprising:
   - gossypol (e.g., free gossypol (also known as unbound gossypol that is available for digestion), biologically active gossypol, bioavailable gossypol, racemic gossypol, (+)-gossypol, (−)-gossypol, or any combination thereof); and
   - non-gossypol matter (e.g., non-free gossypol, non-biologically active gossypol, non-bioavailable gossypol, non-racemic gossypol, non-(+)-gossypol, non-(−)-gossypol, or any combination thereof), the non-gossypol matter making up the remainder of the composition after accounting for the gossypol (e.g., free gossypol, biologically active gossypol, bioavailable gossypol, racemic gossypol, (+)-gossypol, (−)-gossypol, or any combination thereof);

optionally the gossypol (e.g., free gossypol, biologically active gossypol, bioavailable gossypol, racemic gossypol, (+)-gossypol, (−)-gossypol, or any combination thereof) makes up 0.00025 to 1.4 wt. % of the composition, 0.005 to 1.4 wt. % of the composition, 0.04 to 0.08 wt. % of the composition, 0.15 to 1.4 wt. % of the composition, 0.35 to 1 wt. % of the composition, 0.4 to 0.9 wt. % of the composition, at least 0.00025, 0.0003, 0.00035, 0.0004, 0.00045, 0.0005, 0.0006, 0.0007, 0.0008, 0.0009, 0.001, 0.002, 0.003, 0.004, 0.005, 0.006, 0.007, 0.0075, 0.0076, 0.0077, 0.0078, 0.0079, 0.008, 0.009, 0.01, 0.02, 0.03, 0.04, 0.05, 0.06, 0.07, 0.08, 0.09, 0.1, 0.11, 0.12, 0.123, 0.13, 0.14, 0.15, 0.16, 0.17, 0.18, 0.19, 0.2, 0.21, 0.22, 0.225, 0.2275, 0.23, 0.24, 0.25, 0.30, 0.35, 0.4, 0.45, 0.5, 0.55, 0.6, 0.65, 0.7, 0.75, 0.8, 0.85, 0.9, 0.95, 1, 1.1, 1.2, or 1.3 wt. % of the composition, no more than 0.00025, 0.0003, 0.00035, 0.0004, 0.00045, 0.0005, 0.0006, 0.0007, 0.0008, 0.0009, 0.001, 0.002, 0.0025, 0.003, 0.004, 0.005, 0.006, 0.007, 0.0075, 0.0076, 0.0077, 0.0078, 0.0079, 0.008, 0.009, 0.01, 0.02, 0.03, 0.04, 0.05, 0.06, 0.07, 0.08, 0.09, 0.1, 0.11, 0.12, 0.123, 0.13, 0.14, 0.15, 0.05, 0.06, 0.07, 0.08, 0.09, 0.1, 0.15, 0.16, 0.17, 0.18, 0.19, 0.2, 0.21, 0.22, 0.225, 0.2275, 0.23, 0.24, 0.25, 0.30, 0.35, 0.4, 0.45, 0.5, 0.55, 0.6, 0.65, 0.7, 0.75, 0.8, 0.85, 0.9, 0.95, 1, 1.1, 1.2, 1.3 or 1.4 wt. % of the composition, or any combination thereof;

optionally the free gossypol makes up 0.00025 to 1.4 wt. % of the composition, 0.005 to 1.4 wt. % of the composition, 0.04 to 0.08 wt. % of the composition, 0.15 to 1.4 wt. % of the composition, 0.35 to 1 wt. % of the composition, 0.4 to 0.9 wt. % of the composition, at least 0.00025, 0.0003, 0.00035, 0.0004, 0.00045, 0.0005, 0.0006, 0.0007, 0.0008, 0.0009, 0.001, 0.002, 0.0025, 0.003, 0.004, 0.005, 0.006, 0.007, 0.008, 0.009, 0.01, 0.02, 0.03, 0.04, 0.05, 0.06, 0.07, 0.08, 0.09, 0.1, 0.11, 0.12, 0.123, 0.13, 0.14, 0.15, 0.2, 0.25, 0.30, 0.35, 0.4, 0.45, 0.5, 0.55, 0.6, 0.65, 0.7, 0.75, 0.8, 0.85, 0.9, 0.95, 1, 1.1, 1.2, or 1.3 wt. % of the composition, no more than 0.00025, 0.0003, 0.00035, 0.0004, 0.00045, 0.0005, 0.0006, 0.0007, 0.0008, 0.0009, 0.001, 0.002, 0.0025, 0.003, 0.004, 0.005, 0.006, 0.007, 0.008, 0.009, 0.01, 0.02, 0.03, 0.04, 0.05, 0.06, 0.07, 0.08, 0.09, 0.1, 0.11, 0.12, 0.123, 0.13, 0.14, 0.15, 0.05, 0.06, 0.07, 0.08, 0.09, 0.1, 0.15, 0.2, 0.25, 0.30, 0.35, 0.4, 0.45, 0.5, 0.55, 0.6, 0.65, 0.7, 0.75, 0.8, 0.85, 0.9, 0.95, 1, 1.1, 1.2, 1.3 or 1.4 wt. % of the composition, or any combination thereof;

optionally the non-gossypol matter comprises a portion of cottonseed meal that is not gossypol;

optionally the non-gossypol matter comprises a bulk feed component (e.g., a bulk feed component that is not the non-gossypol portion of cottonseed meal);

optionally the non-gossypol matter comprises an effective amount of pig attractant;

optionally the non-gossypol matter comprises an effective amount of a flavored component;

optionally the non-gossypol matter comprises a coating for the composition; and optionally the total amount of the composition (e.g., in a serving, in a package or plurality of packages, in a delivery apparatus or system or combination thereof) is at least the average amount that a male feral pig eats for one meal (e.g. at a location where the composition will be located), at least 2, 3, 4, 5, 6, 7, 8, 9, 10, 20, 30, 40, 50, 60, 70, 80, or 90 times the average amount that a pig (e.g., male pig, female pig, or male and female pigs) eats for one meal (e.g., at a location where the composition will be located), no more than 3, 4, 5, 6, 7, 8, 9, 10, 20, 30, 40, 50, 60, 70, 80, 90 or 100 times the average amount that a pig (e.g., male pig, female pig, or male and female pigs) eats for one meal (e.g., at a location where the composition will be located), is 3 to 5 lbs, is 3 to 200 lbs, is at least 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 150, 200 lbs, is no more than 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 150, 200 lbs, or any combination thereof 2. The composition of clause 1, the composition comprising cottonseed extract (e.g., cottonseed oil, crude cottonseed oil, refined cottonseed oil or any combination thereof);

optionally the cottonseed extract comprising at least a portion, all of the gossypol or a portion of the gossypol (e.g., free gossypol, biologically active gossypol, bioavailable gossypol, racemic gossypol, (+)-gossypol, (−)-gossypol, or any combination thereof);

optionally the cottonseed extract (e.g., cottonseed oil, crude cottonseed oil, refined cottonseed oil or any combination thereof) makes up at least 0.5, 0.6, 0.7, 0.8, 0.9, 1.0, 1.1, 1.2, 1.3, 1.4, 1.5, 1.6, 1.7, 1.8, 1.9, 2, 2.5, 3, 3.5, 4, 4.5 or 5 wt. % of the composition; no more than 0.5, 0.6, 0.7, 0.8, 0.9, 1.0, 1.1, 1.2, 1.3, 1.4, 1.5, 1.6, 1.7, 1.8, 1.9, 2, 2.5, 3, 3.5, 4, 4.5 or 5 wt. % of the composition; or any combination thereof;

optionally the cottonseed extract (e.g., cottonseed oil, crude cottonseed oil, solvent-extracted cottonseed oil, screw-pressed oil, refined cottonseed oil or any combination thereof) comprises at least 0.025, 0.03, 0.035, 0.04, 0.045, 0.05, 0.055, 0.06, 0.065, 0.07, 0.075, 0.1, 0.11, 0.12, 0.123, 0.13, 0.14, 0.15, 0.16, 0.17, 0.18, 0.19, 0.2, 0.201, 0.202, 0.203, 0.204, 0.205, 0.206, 0.207, 0.208, 0.209, 0.21, 0.22, 0.23, 0.24, 0.25, 0.26, 0.27, 0.28, 0.29, 0.3, 0.4, 0.41, 0.42, 0.43, 0.44, 0.45, 0.46, 0.47, 0.48, 0.49, 0.5, 0.54, 0.55, 0.6, 0.7, 0.75, 0.79, or 0.8 wt. % gossypol; no more than 0.025, 0.03, 0.035, 0.04, 0.045, 0.05, 0.055, 0.06, 0.065, 0.07, 0.075, 0.1, 0.11, 0.12, 0.123, 0.13, 0.14, 0.15, 0.16, 0.17, 0.18, 0.19, 0.2, 0.201, 0.202, 0.203, 0.204, 0.205, 0.206, 0.207, 0.208, 0.209, 0.21, 0.22, 0.23, 0.24, 0.25, 0.26, 0.27, 0.28, 0.29, 0.3, 0.4, 0.41, 0.42, 0.43, 0.44, 0.45, 0.46, 0.47, 0.48, 0.49, 0.5, 0.54, 0.55, 0.6, 0.7, 0.75, 0.79, or 0.8 wt. % gossypol; or any combination thereof; optionally the gossypol being free gossypol, biologically active gossypol, bioavailable gossypol, racemic gossypol, (+)-gossypol, (−)-gossypol, or any combination thereof; optionally the cottonseed extract is not alkali-refined cottonseed oil, is not bleached cottonseed oil, or is not both alkali-refined and bleached cottonseed oil;

optionally the cottonseed oil, the crude cottonseed oil, the refined cottonseed oil or any combination thereof comprises at least 0.025, 0.03, 0.035, 0.04, 0.045, 0.05, 0.055, 0.06, 0.065, 0.07, 0.075, 0.1, 0.11, 0.12, 0.123, 0.13, 0.14, 0.15, 0.16, 0.17, 0.18, 0.19, 0.2, 0.201, 0.202, 0.203, 0.204, 0.205, 0.206, 0.207, 0.208, 0.209, 0.21, 0.22, 0.23, 0.24, 0.25, 0.26, 0.27, 0.28, 0.29, 0.3, 0.4, 0.41, 0.42, 0.43, 0.44, 0.45, 0.46, 0.47, 0.48, 0.49, 0.5, 0.54, 0.55, 0.6, 0.7, 0.75, 0.79, or 0.8 wt. % gossypol; no more than 0.025, 0.03, 0.035, 0.04, 0.045, 0.05, 0.055, 0.06, 0.065, 0.07, 0.075, 0.1, 0.11, 0.12, 0.123, 0.13, 0.14, 0.15, 0.16, 0.17, 0.18, 0.19, 0.2, 0.201, 0.202, 0.203, 0.204, 0.205, 0.206, 0.207, 0.208, 0.209, 0.21, 0.22, 0.23, 0.24, 0.25, 0.26, 0.27, 0.28, 0.29, 0.3, 0.4, 0.41, 0.42, 0.43, 0.44, 0.45, 0.46, 0.47, 0.48, 0.49, 0.5, 0.54, 0.55, 0.6, 0.7, 0.75, 0.79, or 0.8 wt. % gossypol; or any combination thereof; optionally the gossypol being free gossypol, biologically active gossypol, bioavailable gossypol, racemic gossypol, (+)-gossypol, (−)-gossypol, or any combination thereof and optionally the cottonseed extract makes up 0.005 to 5 wt. % of the composition, 1 to 5 wt. % of the composition, 0.005 to 1.4 wt. % of the composition, 0.04 to 0.08 wt. % of the composition, 0.15 to 1.4 wt. % of the composition, 0.35 to 1 wt. % of the composition, 0.4 to 0.9 wt. % of the composition, at least 0.005, 0.006, 0.007, 0.008, 0.009, 0.01, 0.02, 0.03, 0.04, 0.05, 0.06, 0.07, 0.08, 0.09, 0.1, 0.11, 0.12, 0.13, 0.14, 0.15, 0.2, 0.25, 0.30, 0.35, 0.4, 0.45, 0.5, 0.55, 0.6, 0.65, 0.7, 0.75, 0.8, 0.85, 0.9, 0.95, 1, 1.1, 1.2, 1.3, 1.4, 1.5, 1.6, 1.7, 1.8, 1.9, 2, 2.5, 3, 3.5, 4, 4.5 or 5 wt. % of the composition, no more than 0.006, 0.007, 0.008, 0.009, 0.01, 0.02, 0.03, 0.04, 0.05, 0.06, 0.07, 0.08, 0.09, 0.1, 0.11, 0.12, 0.13, 0.14, 0.15, 0.05, 0.06, 0.07, 0.08, 0.09, 0.1, 0.15, 0.2, 0.25, 0.30, 0.35, 0.4, 0.45, 0.5, 0.55, 0.6, 0.65, 0.7, 0.75, 0.8, 0.85, 0.9, 0.95, 1, 1.1, 1.2, 1.3, 1.4, 1.5, 1.6, 1.7, 1.8, 1.9, 2, 2.5, 3, 3.5, 4, 4.5 or 5 wt. % of the composition, or any combination thereof.

3. The composition of any preceding clause, the composition comprising cottonseed meal, optionally the cottonseed meal comprising all or a portion of the gossypol and the non-gossypol matter comprising the portion of the cotton seed meal that is not gossypol; optionally the cottonseed meal makes up (i) 5 to 75 wt. % of the composition, (ii) 5 to 60 wt. % of the composition, (iii) 15 to 70 wt. % of the composition, (iv) 25 to 50 wt. % or 35 to 50 wt. % of the composition, (v) 38.8 to 41.2 wt. % or 40 to 45 wt. % of the composition, (vi) at least 5, 10, 15, 20, 25, 30, 35, 36, 37, 38, 38.8, 39, 40, 41, 41.2, 42, 43, 44, 45, 46, 47, 48, 49, 50, 55, 60, 65 or 70 wt. % of the composition, (vii) no more than 10, 15, 20, 25, 26, 27, 28, 29, 30, 35, 36, 37, 38, 38.8, 39, 40, 41, 41.2, 42, 43, 44, 45, 46, 47, 48, 49, 50, 55, 60, 65, 70 or 75 wt. % of the composition, or (viii) any combination thereof; optionally the cottonseed meal comprises 0.123 wt. % gossypol or 0.1 to 0.2 wt. % gossypol or 0.057 to 0.238 wt. % gossypol (e.g., optionally the gossypol is free gossypol, biologically active gossypol, bioavailable gossypol, racemic gossypol, (+)-gossypol, (−)-gossypol, or any combination thereof); and optionally the cottonseed meal comprises at least 0.03, 0.04, 0.05, 0.055, 0.056, 0.057, 0.058, 0.059, 0.06, 0.07, 0.09, 0.1, 0.11, 0.12, 0.121, 0.122, 0.123, 0.124, 0.125, 0.13, 0.14, 0.15, 0.16, 0.17, 0.18, 0.19, 0.2, 0.21, 0.22, 0.23, 0.235, 0.236, 0.237, 0.238, 0.239, 0.24, or 0.25 wt. % gossypol; no more than 0.03, 0.04, 0.05, 0.055, 0.056, 0.057, 0.058, 0.059, 0.06, 0.07, 0.09, 0.1, 0.11, 0.12, 0.121, 0.122, 0.123, 0.124, 0.125, 0.13, 0.14, 0.15, 0.16, 0.17, 0.18, 0.19, 0.2, 0.21, 0.22, 0.23, 0.235, 0.236, 0.237, 0.238, 0.239, 0.24, or 0.25 wt. % gossypol; or any combination thereof; optionally the gossypol being free gossypol, biologically active gossypol, bioavailable gossypol, racemic gossypol, (+)-gossypol, (−)-gossypol, or any combination thereof 4. The composition of any preceding clause:

wherein the effective amount of pig attractant (e.g., scented component, pig pheromone, or any combination thereof) is a concentration of the pig attractant in the composition that is configured to attract the pig to the composition, induce the pig to eat the composition or a combination thereof;

wherein the effective amount of the pig attractant (e.g., scented component, pig pheromone, or any combination thereof) is a concentration of the pig attractant in the composition that is configured to mask the presence of gossypol in the composition sufficiently to attract the pig to the composition, induce a pig (e.g., male pig, female pig, or male and female pigs) to eat the composition, or any combination thereof;

wherein the effective amount of flavored component is a concentration of the flavored component in the composition that is configured to provide the composition with a flavor that is desirable to the pig, to induce the pig to eat the composition or a combination thereof;

wherein the effective amount of the flavored component is a concentration of the flavored component in the composition that is configured to mask the presence of gossypol in the composition sufficiently so that the composition is desirable to the pig, to induce a pig to eat the composition, or any combination thereof;

or any combination thereof.

5. The composition of any preceding clause, wherein the composition is configured to have a bulk density so that the smallest adult pig (e.g., male pig, female pig or male and female pigs) expected to consume the composition will be able to eat at least 3 lbs (and optionally up to 5 lbs) of the composition.

6. The composition of any preceding clause, wherein the composition is configured: (i) to reduce the fertility of the pig after being eaten by the pig, (ii) to be eaten by the pig, and reduce the fertility of the pig after the composition is eaten by the pig, (iii) to attract the pig, induce the pig to eat the composition, and reduce the fertility of the pig after the composition is eaten by the pig, or (iv) any combination thereof.

7. The composition of any preceding clause, wherein the pig is a male pig or wherein the pig is a male or female pig.

8. The composition of any preceding clause, wherein the pig is a female pig or wherein the pig is a male or female pig.

9. The composition of any preceding clause, the composition comprising:

pig attractant;

a flavored component;

or any combination thereof;

optionally wherein the pig attractant comprises a scented component, pig pheromone, or any combination thereof;

optionally wherein the pig attractant, flavored component, or any combination thereof makes up (i) 0.05 to 25 wt. %, 0.05-0.1 wt. % of the composition, (ii) 0.1-0.75 wt. % of the composition, (iii) 0.2-0.5 wt. % of the composition, (iv) 3.99-4.41 wt. % of the composition, (v) at least 0.05, 0.1, 0.15, 0.2, 0.5, 1, 2, 3, 3.5, 3.99, 4.41, 4.5, 5, 10, 15 or 20 wt. % of the composition, (vi) no more than 0.1, 0.15, 0.2, 0.5, 1, 2, 3, 3.5, 3.99, 4.41, 4.5, 5, 10, 15, 20 or 25 wt. % of the composition, or (vii) any combination thereof;

optionally wherein the pig attractant, flavored component or any combination thereof comprises an apple flavor, sour corn mash flavor (e.g., dried sour corn mash), caramel apple flavor, sweet flavor, molasses flavor, berry flavor, fish meal flavor, corn flavor, beet flavor, corn gluten flavor (e.g., corn gluten), creosote flavor, salty and sweet flavor, strawberry flavor, cherry flavor, caramel flavor, diesel flavor, lactose flavor, pheromone (e.g., male hog pheromones, female hog pheromones or any combination thereof), corn steep liquor, or any combination thereof;

optionally the corn steep liquor makes up (i) 3.99 to 4.41 wt. % of the composition, (ii) at least 1, 2, 3, 3.5, 3.6, 3.7, 3.8, 3.9 3.99, 4, 4.1, 4.2, 4.3, 4.4, 4.41, 4.5, 4.6, 4.7, 4.8, 4.9, 5, or 10 wt. % of the composition, (iii) no more than 1, 2, 3, 3.5, 3.6, 3.7, 3.8, 3.9, 3.99, 4.0, 4.1, 4.2, 4.3, 4.4, 4.41, 4.5, 4.6, 4.7, 4.8, 4.9, 5, or 10 wt. % of the composition, or (iv) any combination thereof;

optionally the apple flavor makes up 0.05 to 0.75 wt. % of the composition, at least 0.05, 0.1, 0.2, 0.3, 0.4, 0.5, 0.6 or 0.7 wt. % of the composition, no more than 0.1, 0.2, 0.3, 0.4, 0.5, 0.6, 0.7 or 0.75 wt. % of the composition, or any combination thereof; and optionally the sour corn mash flavor (e.g., dried sour corn mash) makes up 0.25 to 25 wt. % of the composition, at least 0.25, 0.5, 1, 2, 3. 4, 5, 10, 15, or 20 wt. % of the composition, no more than 0.5, 1, 2, 3. 4, 5, 10, 15, 20 or 25 wt. % of the composition or any combination thereof.

10. The composition of any preceding clause, comprising:

at least one additive (e.g., as a portion of the bulk feed component, pig attractant, flavored component, scented component, pig pheromone, or any combination thereof);

optionally wherein the at least one additive comprises calcium carbonate, dried whey, flaxseed, flaxseed meal, green tea extract, cheese meal, or any combination thereof; and optionally wherein the additive component makes up 0.05-5 wt. % of the composition, 1-4 wt. % of the composition, 2-3 wt. % of the composition, at least 0.05, 0.1, 0.5, 1, 2, 3 or 4 wt. % of the composition, no more than 0.1, 0.5, 1, 2, 3, 4, or 5 wt. % of the composition, or any combination thereof.

11. The composition of any preceding clause, wherein the coating comprises:

starch, optionally, corn starch; and optionally wherein all or any selection of the other components of the composition are coated with the starch; and optionally wherein all the components of the composition, any component of the composition, any combination of the components of the composition, or the cottonseed extract is sprayed with a misted form of starch (e.g., corn starch) to provide a coated composition having the coating, the coated composition is dried to provide a dried coated composition, and the dried coated composition is broken into smaller pieces (e.g., chunks and/or granules), thereby giving the smaller pieces a more rigid structure compared to the composition without the coating, and thereby protecting the composition when the composition is exposed to an environment, for example a natural environment, optionally, when the composition is placed in a field.

12. The composition of any preceding clause, wherein the composition comprises:

corn;

optionally wherein the bulk feed component comprises the corn;

optionally wherein the corn comprises cracked corn, kernel corn, ground corn, corn meal, field corn, or a combination thereof; and optionally wherein the corn makes up (i) 5 to 75 wt. % of the composition, (ii) 25-65 wt. % of the composition, (iii) 35-50 wt. % of the composition, (iv) 45-55 wt. % of the composition, (v) 48.5-51.5 wt. % of the composition, (vi) at least 5, 10, 15, 20, 25, 30, 35, 40, 45, 46, 47, 48, 48.5, 49, 50, 51.5, 55, 60, 65 or 70 wt. % of the composition, (vii) no more than 10, 15, 20, 25, 30, 35, 40, 45, 46, 47, 48, 48.5, 49, 50, 51.5, 55, 60, 65, 70 or 75 wt. % of the composition, or (viii) any combination thereof.

13. The composition of any preceding clause, wherein the composition comprises:

corn gluten;

optionally wherein the bulk feed component comprises the corn gluten;

optionally wherein the corn gluten comprises powdered corn gluten, pelleted corn gluten, ground corn gluten, corn gluten meal, wet corn gluten, or a combination thereof; and optionally wherein the corn gluten makes up (i) 1-65 wt. % of the composition, (ii) 25-65 wt. % of the composition, (iii) 35-50 wt. % of the composition, (iv) 45-55 wt. % of the composition, (v) at least 0.5, 0.6, 0.7, 0.8, 0.9, 1, 1.1, 1.2, 1.3, 1.4, 1.5, 2, 3, 4, 5, 10, 15, 20, 25, 30, 35, 40, 45, 50, 55, or 60 wt. % of the composition, (vi) no more than 0.5, 0.6, 0.7, 0.8, 0.9, 1, 1.1, 1.2, 1.3, 1.4, 1.5, 2, 3, 4, 5, 10, 15, 20, 25, 30, 35, 40, 45, 50, 55, 60 or 65 wt. % of the composition, or (vii) any combination thereof.

14. The composition of any preceding clause, wherein the composition comprises:

beet pulp;

optionally wherein the bulk feed component comprises the beet pulp;

optionally wherein the beet pulp comprises wet beet pulp, dried beet pulp, sliced beet pulp, pelleted beet pulp, or a combination thereof; and optionally wherein the beet pulp makes up 25-65 wt. % of the composition, 35-50 wt. % of the composition, 45-55 wt. % of the composition, at least 25, 30, 35, 40, 45, 50, 55, or 60 wt. % of the composition, no more than 30, 35, 40, 45, 50, 55, 60 or 65 wt. % of the composition, or any combination thereof.

15. The composition of any preceding clause, wherein the composition comprises:

salt (e.g., sodium chloride);

optionally wherein the salt forms at least a portion of the pig attractant, flavored component, scented component, pig pheromone, or any combination thereof; and optionally wherein the salt makes up (i) 0.5-4.0 wt. % of the composition, (ii) 1.0-3.0 wt. % of the composition, (iii) 2.0-2.5 wt. % of the composition, (iv) at least 0.5, 1, 1.5, 1.6, 1.7, 1.8, 1.9, 2, 2.1, 2.2, 2.3, 2.4, 2.5, 3 or 3.5 wt. % of the composition, (v) no more than 1, 1.5, 1.9, 2, 2.1, 2.5, 3, 3.5 or 4 wt. % of the composition, or (vi) any combination thereof.

16. The composition of any preceding clause, wherein the composition comprises:

molasses (e.g., cane molasses);

optionally wherein the molasses forms at least a portion of the pig attractant, flavored component, scented component, pig pheromone, or any combination thereof; and optionally wherein the molasses makes up (i) 0.5 to 7 wt. % of the composition, (ii) 0.5 to 5 wt. % of the composition, (iii) 2.5-7.0 wt. % of the composition, (iv) 3.0-6.0 wt. % of the composition, (v) 3.5-5.0 wt. % of the composition, (vi) at least 0.5, 1, 1.5, 1.6, 1.7, 1.71, 1.8, 1.89, 1.9, 2, 2.5, 3, 3.5, 4, 4.5, 5, 5.5, 6, or 6.5 wt. % of the composition, (vii) no more than 1, 1.5, 1.6, 1.7, 1.71, 1.8, 1.89, 1.9, 2, 2.5, 3, 3.5, 4, 4.5, 5, 5.5, 6, 6.5 or 7 wt. % of the composition, or (viii) any combination thereof.

17. The composition of any preceding clause, wherein the composition comprises:

lactose;

optionally wherein the lactose forms at least a portion of the pig attractant, flavored component, scented component, pig pheromone, or any combination thereof;

optionally wherein the lactose comprises powdered lactose, granulated lactose, liquid lactose, or a combination thereof; and optionally wherein the lactose makes up 2.0-10 wt. % of the composition, 3.5-7.5 wt. % of the composition, 4.5-6.0 wt. % of the composition, at least 2, 2.5, 3, 3.5, 4, 4.5, 5, 5.5, 6, 6.5, 7, 7.5, 8, 8.5, 9, or 9.5 wt. % of the composition, no more than 2.5, 3, 3.5, 4, 4.5, 5, 5.5, 6, 6.5, 7, 7.5, 8, 8.5, 9, 9.5 or 10 wt. % of the composition, or any combination thereof.

18. The composition of any preceding clause, wherein one or any combination of the components of the composition is provided in a form that is ground, pelleted, powdered, liquid, oil (e.g., cotton seed extract, cottonseed oil, crude cottonseed oil, refined cottonseed oil or any combination thereof), cracked, a meal, or any combination thereof.

19. The composition of any preceding clause, wherein the composition is processed or packaged to retain contraceptive effectiveness after prolonged storage without refrigeration (e.g., at 25° C. at 1 atm pressure) for at least 1, 2, 3, 4, or 5 months and optionally up to 2, 3, 4, 5 or 6 months under dry storage conditions (e.g., 50% relative humidity) without exposure to direct sunlight, water, rain, or flowing water (e.g., placed in a storage unit with the specified conditions); wherein contraceptive effectiveness means capable of rendering a viable breeding pig (e.g., male pig, female pig or male or female pig) sterile if the viable breeding pig eats 3 pounds of composition per day for 3 consecutive days, where sterile means that after eating the composition, the pig (e.g., male pig) has a sperm motility score of less than 70%, 65%, 60%, 55%, 50%, 45%, 40%, 35% or 30%, a sperm morphology score of less than 80%, 75%, 70%, 65%, 60%, 55%, 50%, 45%, 40%, 35%, or 30%, or a combination thereof.

20. The composition of any preceding clause wherein the composition is processed or packaged to be shelf stable for 1, 2, 3, 4, or 5 months and up to 6 months during unrefrigerated storage in a dry storage place without exposure to direct sunlight, water, rain, or flowing water.

21. The composition of any preceding clause wherein feed is stable and effective, in an enclosed pig-only feeder (e.g. wild- or feral-pig-only feeder) for 1, 2, or 3 months and up to 4 months, without exposure to direct sunlight, water, rain, or flowing water.

22. The composition of any preceding clause:

wherein the composition is a dry food, having a moisture content of 10-40 wt. %, 10-30 wt. %, 10-20 wt. %, 10-15 wt. %, at least 10, 15, 20, 25, 30, or 35 wt. %, no more than 15, 20, 25, 30, 35 or 40 wt. % or any combination thereof;

wherein the composition has a moisture content equal to 10 to 40 wt. % moisture, at least 10, 15, 20, 25, 30, or 35 wt. % moisture, no more than 15, 20, 25, 30, 35 or 40 wt. % moisture, or any combination thereof;

wherein the composition is 60 to 90 wt. % dry matter, at least 60, 65, 70, 75, 80 or 85 wt. % dry matter, no more than 90, 85, 80, 75, 70 or 65 wt. % dry matter, or any combination thereof; or any combination thereof.

23. An assembly comprising:

the composition of any preceding clause; and a package (e.g., for the composition);

optionally wherein the package at least partially or completely encloses the composition; optionally wherein the package encloses at least 10, 20, 30, 40, 50, 60, 70, 80, 90, 91, 92, 93, 94, 95, 96, 97, 98, 99, or 100% by mass, volume or surface area of the composition; no more than 20, 30, 40, 50, 60, 70, 80, 90, 91, 92, 93, 94, 95, 96, 97, 98, 99 or 100% of the composition by mass, volume or surface area; or any combination thereof 24. The assembly of any preceding clause, wherein the package is a plastic package;

wherein the package is a poly weave package;

wherein the package is a paper package;

or any combination thereof.

25. The assembly of any preceding clause, wherein the assembly comprises:

a suggestion (e.g., written suggestion, optionally on the package or on a separate sheet), a recommendation (e.g., written recommendation, optionally on the package or on a separate sheet) or instruction (e.g., written instruction, optionally on the package or on a separate sheet) to place the composition in a feeder (e.g., pig-specific feeder).

26. The assembly of any preceding clause, wherein the composition (e.g., inside the package) has a moisture content equal to 10 to 40 wt. % moisture; at least 10, 15, 20, 25, 30, or 35 wt. % moisture; no more than 15, 20, 25, 30, 35 or 40 wt. % moisture; or any combination thereof; or wherein the composition (e.g., inside the package) is 60 to 90 wt. % dry matter, at least 60, 65, 70, 75, 80 or 85 wt. % dry matter; no more than 90, 85, 80, 75, 70 or 65 wt. % dry matter; or any combination thereof; or any combination thereof.

27. A system for delivering an orally ingestible contraceptive composition to a pig (e.g., male pig, female pig, or male or female pig) or a plurality of pigs (e.g., male pigs, female pigs or male and female pigs), the system comprising:

the composition of any preceding clause or the assembly of any preceding clause; and an apparatus configured to permit a pig to eat the composition and inhibit other animals from eating the composition, optionally wherein the other animals comprise deer, felines, canines, rabbits, rodents, birds, reptiles, marsupials, racoons, armadillos, or any combination thereof.

28. The system of any preceding clause, wherein the apparatus is configured to be pig-specific delivery system (e.g., a wild- or feral-pig-specific delivery system) for the composition.

29. The system of any preceding clause, optionally wherein the apparatus is configured to exclude non-hoofed animals from an interior of the apparatus, the interior being configured to contain the composition, and optionally wherein the apparatus is configured to permit pigs (e.g., essentially exclude all other land-based vertebrates (not including animals with opposable thumbs and humans) and only permit pigs) to enter or access an interior of the apparatus, the interior being configured to contain the composition.

30. A method for delivering an orally ingestible contraceptive composition to a pig, the method comprising:

making the composition or the assembly of any preceding clause available to a pig (e.g., in a pig-specific delivery system), and optionally making the composition or the assembly available to the pig using the apparatus or system of any preceding clause.

31. The method of any preceding clause, wherein the method comprises:

permitting the pig to eat the composition.

32. The method of any preceding clause, wherein the method comprises:

using a pig attractant, flavored component, scented component, pig pheromone, or any combination thereof to attract the pig to the composition.

33. The method of any preceding clause, wherein the method comprises:

using a pig attractant, flavored component, scented component, pig pheromone, or any combination thereof to attract the pig to the composition.

to induce the pig to eat the composition.

34. The method of any preceding clause, wherein the method comprises:

reducing the fertility of the pig after the pig eats the composition.

35. The method of any preceding clause, wherein the pig is a wild pig.

36. The method of any preceding clause, wherein the pig is a feral pig.

37. The method of any preceding clause, wherein the pig is a male pig or wherein the pig is a female or male pig.

38. The method of any preceding clause, wherein the pig is a wild or feral pig of domesticated pig breed decent.

39. The method of any preceding clause, wherein the pig is a cross-breed between a feral pig and a pig of domesticated pig breed descent.

40. The method of any preceding clause, wherein the pig is a female pig or wherein the pig is a female or male pig.

41. The method of any preceding clause, wherein the pig is a male pig and as a result of eating the contraceptive composition, the pig has a sperm motility score of 0% to less than 70%, a sperm motility score of at least 0%, 5%, 10%, 15%, 20%, 25%, 30%, 35%, 40%, 45%, 50%, 55%, 60%, or 65%, a sperm motility score of less than 70%, 65%, 60%, 55%, 50%, 45%, 40%, 35% or 30%, or any combination thereof; a sperm morphology score of 0% to less than 80%, a sperm morphology score of at least 0%, 5%, 10%, 15%, 20%, 25%, 30%, 35%, 40%, 45%, 50%, 55%, 60%, 65%, 70%, or 75%, a sperm morphology score of less than 80%, 75%, 70%, 65%, 60%, 55%, 50%, 45%, 40%, 35%, or 30%, or any combination thereof; or any combination thereof.

42. The method of any preceding clause, wherein the pig is a male pig and after eating 3 pounds of contraceptive per day for 3 days in a one month time period, the pig has: a sperm motility score of 0% to less than 70%, a sperm motility score of at least 0%, 5%, 10%, 15%, 20%, 25%, 30%, 35%, 40%, 45%, 50%, 55%, 60%, or 65%, a sperm motility score of less than 70%, 65%, 60%, 55%, 50%, 45%, 40%, 35% or 30%, or any combination thereof; a sperm morphology score of 0% to less than 80%, a sperm morphology score of at least 0%, 5%, 10%, 15%, 20%, 25%, 30%, 35%, 40%, 45%, 50%, 55%, 60%, 65%, 70%, or 75%, a sperm morphology score of less than 80%, 75%, 70%, 65%, 60%, 55%, 50%, 45%, 40%, 35%, or 30%, or any combination thereof; or any combination thereof;

optionally wherein the days are consecutive, optionally wherein the 3 days are nonconsecutive.

43. The method of any preceding clause, wherein the male pig is a feral pig.

44. The method of any preceding clause, wherein the female pig is a feral pig.

45. The method of any preceding clause, wherein the step of making the contraceptive composition available comprises placing the contraceptive into a feeder that selectively allows pigs to eat the contraceptive composition.

46. The method of any preceding clause, wherein the step of making the contraceptive composition available comprises placing the contraceptive composition into an apparatus that permits pigs to eat the contraceptive composition and inhibits other animals from eating the contraceptive composition.

47. The method of any preceding clause:

wherein the morphology of the sperm of the pig is degraded to the point of non-viability;

wherein the sperm of the pig loses the ability to reach and penetrate an egg;

wherein the sperm of the pig does not swim properly;

wherein the pig becomes infertile;

wherein the fertility of the pig is decreased; or any combination thereof.

48. The method of any preceding clause, wherein the apparatus is a pig specific delivery system (e.g., wild or feral pig specific delivery system) or a pig specific delivery system (e.g., wild or feral pig specific delivery system) that is presently available and approved for use by the entity with jurisdiction over the area where the pig specific delivery system will be used.

49. The method of any of preceding clause wherein the composition is protected from an environment (e.g., ambient conditions, rain, sun, wind, or any combination thereof) by packaging, optionally by packaging the composition in plastic or poly weave feed bags.

50. The method of any preceding clause, the method comprising:

spraying starch (e.g., corn starch) on all the components of the composition, any component of the composition, any combination of the components of the composition, or the cottonseed extract to provide a coated composition having the coating;

drying the coated composition to provide a dried coated composition; and breaking the dried coated composition into smaller pieces (e.g., chunks and/or granules), optionally thereby giving the smaller pieces a more rigid structure compared to the composition without the coating, and optionally thereby protecting the composition when the composition is exposed to an environment, for example a natural environment, and optionally, when the composition is placed in a field.

Although embodiments have been described using specific compositions comprising gossypol, additional embodiments can be formed by providing a composition with essentially any formulation comprising gossypol. Additionally, in some embodiments, the composition, excluding gossypol, can comprise various relative proportions of any one component relative to another component, from 0 wt. % to 100 wt. % or any real value or range contained therein. For example, the relative proportions can be selected so that the composition is configured to attract a pig, induce the pig to eat the composition, retain contraceptive effectiveness after placement in situ, and cause reduced fertility or effective sterility of pigs (e.g., male pigs, female pigs or male or female pigs) when at least 3 lbs of the composition is consumed each day by a pig (e.g., male pig, female pig or male or female pig) for 3 consecutive days, or any combination thereof.

Although embodiments have been described using the term "comprising" or its conjugates, additional embodiments can be created by replacing the term "comprising" with "consisting essentially of" or "consisting of" and their conjugates. Additional embodiments can also be created by replacing "comprising" or its conjugates with "comprising at least 1, 2, 3, 4, 5, 10, 20, 30, 40, 50, 60, 70, 80, 90, 95, 96, 97, 98, or 99 wt. % and up to 100 wt. %" or its conjugates.

Although embodiments have been described using the term "substantially," additional embodiment can be formed in which the term "substantially" is replaced by "mostly' or "at least 50, 60, 70, 80, 90, 95, 96, 97, 98, or 99% and up to 100%."

Although embodiments have been described using a first range having a first set of end points, additional embodiments can be created by replacing the first range with a narrower range having endpoints that are selected from any value contained in the first range.

When an ostensibly open-ended range is described in this disclosure using the terms "at least," "more than," "less than," "no more than" or similar terms, the range includes all possible values for the open-ended range, but excludes values that are not physically possible. For example, if the range can only include values up to 100% in context, then values larger than 100% are not included in the range. As another example, if the range can only include values down to 0% in context, then values smaller than 0% are not included in the range. Similarly, if the range can only include positive values in context, then negative values are excluded from the range.

For embodiments described in this disclosure as including optional elements, this means that one or any combination of the optional elements can be included in the embodiments, but are not required to be included. For example, some of the embodiments can incorporate none of the optional elements, some of the embodiments can incorporate one and only one of the optional elements; some of the embodiments can incorporate any selection of a plurality of the optional elements; and some of the embodiments can incorporate all of the optional elements.

Additionally, while this invention has been particularly shown and described with reference to preferred embodiments, it will be understood by those skilled in the art that various changes in form and detail may be made therein without departing from the spirit and scope of the invention. The inventors expect skilled artisans to employ such variations as appropriate, and the inventors intend the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

We claim:

1. A system for delivering an orally ingestible contraceptive composition to a pig, the system comprising:

the orally ingestible contraceptive composition, the composition comprising:

0.04 to 0.15 wt. % free gossypol, and non-free-gossypol matter, the non-free-gossypol matter comprising a bulk feed component and a pig attractant or a flavored component or any combination thereof; and an apparatus configured to permit pigs to eat the composition and inhibit other animals from eating the composition.

2. The system of claim 1, wherein the other animals comprise deer, felines, canines, rabbits, rodents, birds, reptiles, marsupials, racoons, armadillos, or any combination thereof.

3. The system of claim 1, wherein the apparatus is configured to exclude non-hoofed animals from an interior of the apparatus, the interior being configured to contain the composition.

4. The system of claim 2, wherein the apparatus is configured to permit pigs to enter or access an interior of the apparatus, the interior being configured to contain the composition.

5. The system of claim 1, wherein the composition comprises cottonseed meal, wherein the cottonseed meal makes up 5 to 60 wt. % of the composition; wherein the cottonseed meal comprises at least a portion of the free gossypol; and wherein the cottonseed meal provides at least a portion of the non-free-gossypol matter.

6. The system of claim 5, wherein the composition comprises the bulk feed component and the bulk feed component comprises corn and the corn makes up 25 to 65 wt. % of the composition.

7. The system of claim 6, wherein the pig attractant, the flavored component or a combination thereof comprises molasses, salt, apple flavor, dried sour corn mash or any combination thereof.

8. The system of claim 7:

wherein the molasses makes up 0.5 to 5 wt. % of the composition;

wherein the salt makes up 0.5 to 4 wt. % of the composition;

wherein the apple flavor makes up 0.05 to 0.75 wt. % of the composition;

wherein the dried sour corn mash makes up 0.25 to 25 wt. % of the composition; or any combination thereof.

9. An assembly comprising:

an orally ingestible contraceptive composition, the composition comprising:

0.04 to 0.15 wt. % free gossypol, and non-free-gossypol matter, the non-free-gossypol matter comprising a bulk feed component and a pig attractant or a flavored component or any combination thereof; and a package that at least partially encloses the composition.

10. The assembly of claim 9, wherein the assembly comprises a written suggestion, recommendation or instruction to place the composition in a feeder.

* * * * *